United States Patent [19]

Klusman

[11] Patent Number: 4,993,874
[45] Date of Patent: Feb. 19, 1991

[54] METHOD AND APPARATUS FOR THE COLLECTION OF REDUCED GASES

[75] Inventor: Ronald W. Klusman, Evergreen, Colo.

[73] Assignee: Colorado School of Mines, Golden, Colo.

[21] Appl. No.: 380,115

[22] Filed: Jul. 14, 1989

[51] Int. Cl.⁵ .............................................. B01D 35/00
[52] U.S. Cl. ................................. 405/128; 73/863.21; 436/178
[58] Field of Search .......................... 405/128, 129, 52; 73/863.23, 864.63, 864.64, 864.65, 863.21, 864; 436/26, 81, 83, 88, 178; 422/88, 83, 101, 102, 99

[56] References Cited

U.S. PATENT DOCUMENTS

| | | | |
|---|---|---|---|
| 1,759,444 | 5/1930 | Dunn et al. | 73/864.66 X |
| 1,993,534 | 3/1935 | Stoltz | 210/164 X |
| 2,203,019 | 6/1940 | Johnson et al. | 73/864.65 |
| 2,345,219 | 3/1944 | Sanderson | 73/863.21 X |
| 3,862,576 | 1/1975 | Pogorski | 436/178 X |
| 3,987,677 | 10/1976 | Alter | 73/863.21 X |
| 4,131,544 | 12/1978 | Elahi | 436/178 X |
| 4,565,786 | 1/1986 | Dunkhase et al. | 436/178 X |
| 4,583,293 | 4/1986 | Smith | 73/864.63 X |
| 4,737,171 | 4/1988 | Courbon | 73/863.21 X |

Primary Examiner—Dennis L. Taylor
Attorney, Agent, or Firm—Richard W. Hanes

[57] ABSTRACT

A method of collecting reduced gases from the soil, water and outdoor and indoor environments but primarily for purposes of mineral, geothermal and petroleum exploration. The method is practiced by isolating a quantity of oxidizing liquid in a container which is constructed to permit selective gaseous communication with an outside environment, then situating the container within a medium containing the gases to be collected and within an airspace contiguous to the medium, then selectively opening the container to gaseous communication with the environment and collecting in the container the reduced gases present in the environment, oxidizing the collected gases in the oxidizing liquid and storing the oxidized gases in aqueous form.

8 Claims, 2 Drawing Sheets

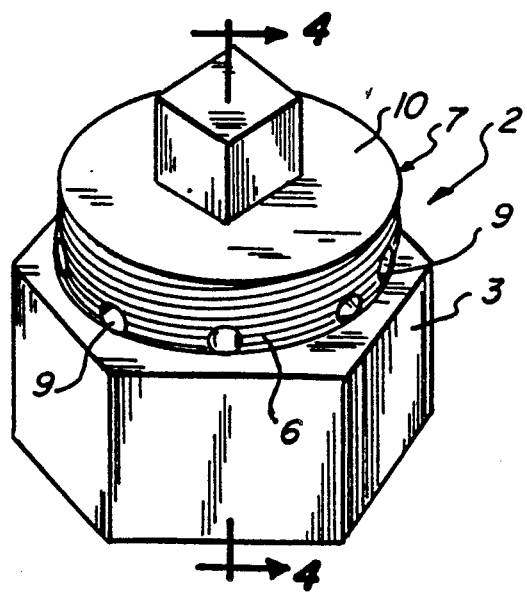
Fig_1
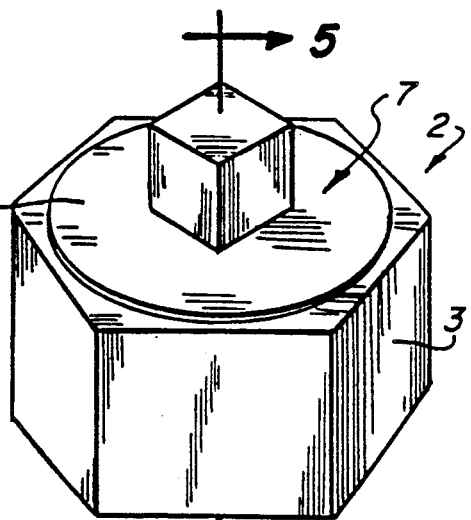
Fig_3
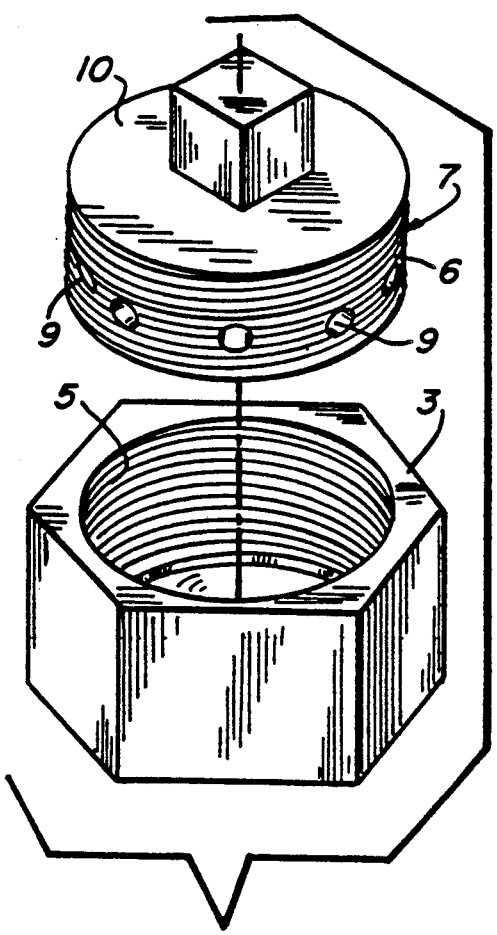
Fig_2
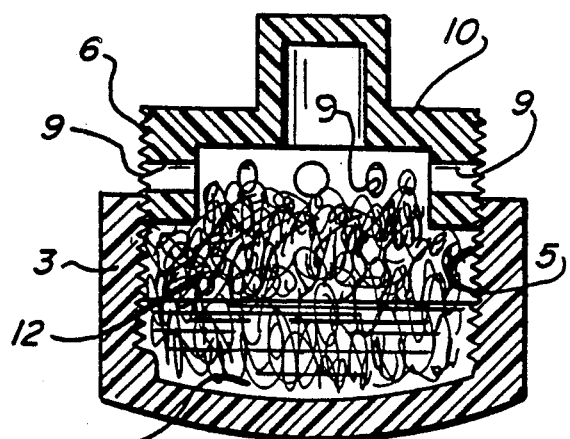
Fig_4
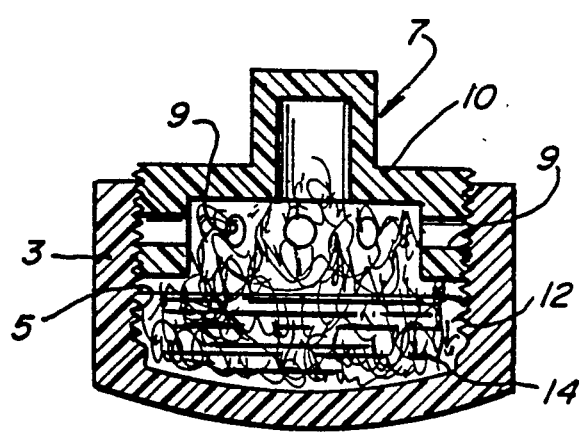
Fig_5

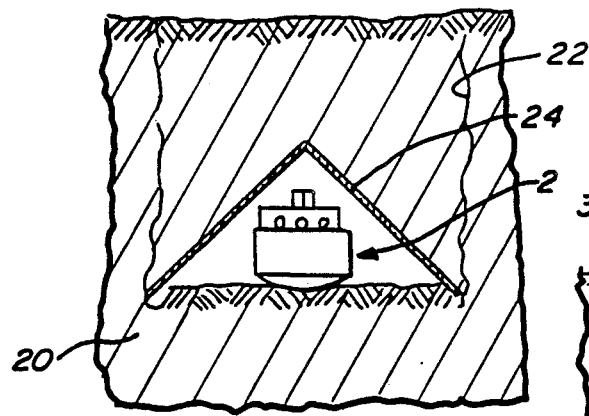
Fig_6
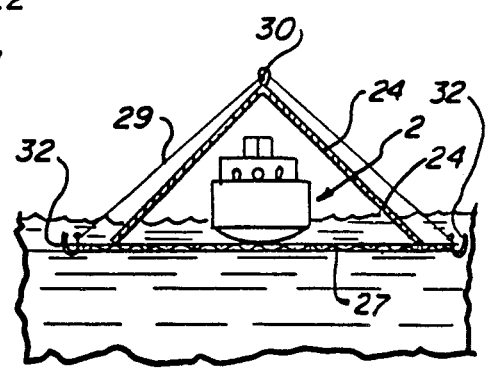
Fig_8
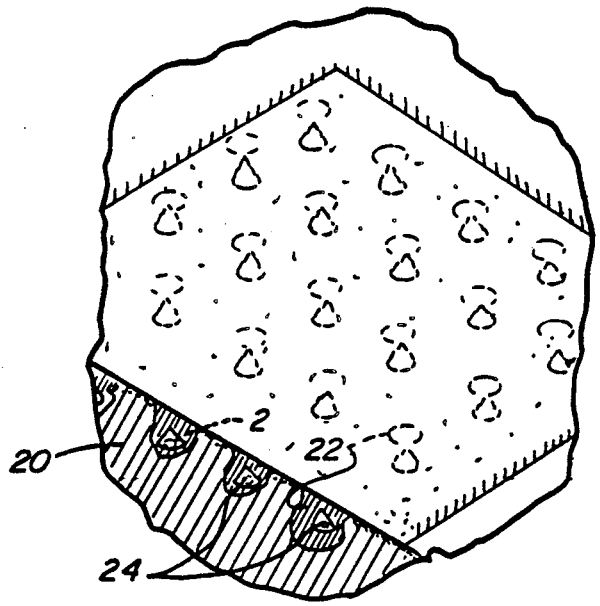
Fig_7
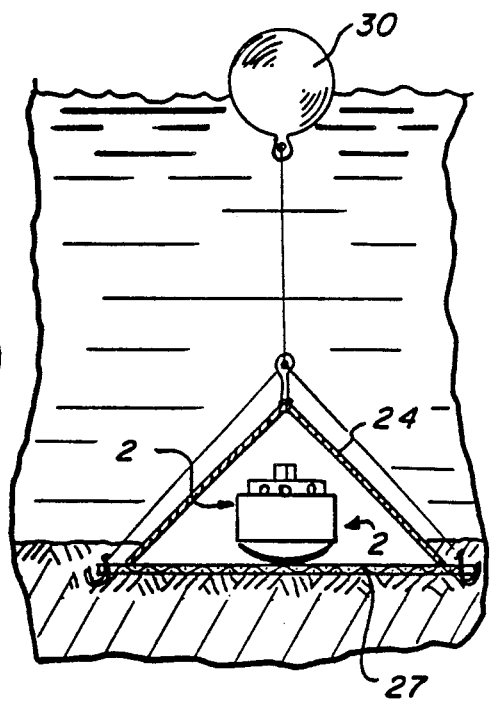
Fig_9

METHOD AND APPARATUS FOR THE COLLECTION OF REDUCED GASES

BACKGROUND OF THE INVENTION

The present invention relates to the process of collecting selected gases from the soil, the outdoor environment and an indoor environment. The method is used to collect that certain class of reduced gases which may be present in low concentrations and difficult to collect for analysis by existing means.

The determination of the presence of reduced gases has applications in mineral, geothermal and petroleum exploration, as well as in several environmental fields. These gases, which are produced by a variety of natural processes in the subsurface, in water or in sediments beneath water bodies, migrate toward the surface of the earth or into the atmosphere, where they can be collected. The presence of anomalous concentrations of these gases in the soil gas, adsorbed on soil particles, or in the atmosphere above the earth's surface can be indicative of deposits of economic interest in the subsurface or of certain types of man-made contamination which may have produced such gases.

THE PRIOR ART

The collection and analysis of gases in the natural and indoor environments is a relatively new field of endeavor which is being effectively applied to a wide variety of problems, primarily in the environmental field and in exploration for natural resources. In many applications, the analysis of the gas or gases of interest requires specialized instrumentation which is not readily transported to the site where the gases exist. In this situation, the gas samples must be collected by some method and transported to the laboratory for analysis.

The use of a pre-evacuated metal container fitted with a gas-tight valve which is opened in the area of interest is one of the first methods used for collecting these types of gases. Other methods have employed large bags made of teflon or other inert material. Where the analytical methods were sufficiently sensitive, smaller sample containers made of metal, glass, or plastic materials have been used and were filled using a syringe. In some cases, the syringe itself was used to store the same, if fitted with a gas-tight valve.

The collection of gases from the subsurface such as exist in soil pores poses additional problems. Common methods include auguring a hole, sealing the hole from the surface with a packer, waiting for equilibrium, then collecting the soil gas sample via a tube which goes through the packer. Another widely used method is to drive a small diameter hollow tube into the ground. The tube has openings in the bottom or sides to allow entry of soil gas into the tube. The gas sample is drawn by a syringe through a septum in the top of the tube and placed in a small pre-evacuated container. These methods are relatively easy but have the disadvantage that they cannot be effectively used if the soil is saturated with water. Generally, large volumes of soil gas cannot be collected using these methods. The hollow tube method is also difficult to use if the soils contain a high proportion of clays.

A difficulty which is always present in the interpretation of soil gas data or in the interpretation of trace gas concentrations in the atmosphere is that concentrations can, and usually do vary significantly over short time periods. The sampling of soil gas over a large area by use of an auger or hollow tube is a process which may take several days to several weeks. The sample collected at a given location represents the composition at the time of collection, but the concentrations of many gases in soils vary significantly over short time periods, exhibiting diurnal as well as seasonal cycles. This fact makes the collected data noisy and difficult to interpret.

An alternative prior art method is to use some type of integrative collection system, that is, a material or method which slowly collects or adsorbs a gas sample over a period of time. This is frequently termed integrative collection. In the case of soil gas sampling, the simplest type of integrative sampling medium is the soil itself. The problem with soil is its natural variability in composition which causes a resultant variability in its ability to adsorb and retain soil gases. The ability of soil to adsorb and retain gases is also a function of the character of the gas of interest and of the ambient soil temperature. Synthetic adsorbents such as charcoal, Tenax, molecular sieve and a variety of man-made materials have been used to eliminate this inherent composition variability in soils and has also been used to collect gases in the atmosphere and in indoor environments.

The integrative collection methods have an advantage in that they tend to smooth out the short term temporal noise, but do not eliminate the longer term seasonal variance observed in the outdoor environment. Integrative collection times are typically in the range of several days to several weeks. This long collection time also gives the integrative method another major advantage, that of sensitivity. Although concentration is not measured directly, the amount collected is proportional to concentration, and measuring variation in concentration over an area is usually of the most value. Integrative methods can give a sensitivity for a trace gas that is not attainable by any other means. The gas adsorbing characteristics of the adsorbent must be known, as it is possible for one gas to replace another previously adsorbed gas if the capacity of the adsorbent is used up. An adsorbent is frequently more effective for one class of gas than another. Integrative collection methods require two trips to the site of collection and cannot result in rapid turnaround of data for interpretation.

While integrative methods are generally successful, there is a particular class of gases of interest in exploration and environmental studies which is difficult to collect and preserve by most integrative methods. These are the reduced gases produced by microbial and some inorganic processes in groundwater and in soils under anaerobic conditions.

Another problem aspect of the integrative collection processes must recognize the fact that if the integrative collection is made in the atmosphere or in the upper part of the soil column, the collected gases are subject to oxidizing conditions. Being thermodynamically unstable in the presence of free oxygen, the gases decompose at varying rates depending on conditions which are generally not known at the sampling site. Fortunately, reduced gases such as volatile hydrocarbons have a higher degree of stability than most other reduced gases and can be adequately collected using adsorbents. However, other reduced gases, such as the hydrides or methylated compounds of non-metallic or semimetallic elements may exhibit limited stability on an adsorbent.

Examples of the reduced gases of interest include methyl sulfide, $CH_3SH$, dimethyl sulfide, $CH_3SCH_3$, carbonyl sulfide, COS, arsine, AsH$_3$, trimethylarsine, As(CH$_3$)$_3$, dimethylselenium, Se(CH$_3$)$_2$ and dimethylmercury, Hg(CH$_3$)$_2$.

Representative literature references include but are not limited to:

Kraner, H. W., "Measurements of the Effects of Atmospheric Variables on the Rn-222 Flux and Soil Gas Concentration." *The Natural Radiation Environment.* J.A.S. Adams, ed., U. Chicago Press, pp. 191–215, 1964.

Tanner, A. B., "Radon Migration In The Ground: A Supplementary Review." *U.S. Geol. Survey, open-file Rept.* 7-1050, 62 p., 1978.

Klusman, R. W. and Webster, J. D., "Meteorological Noise In Crustal Gas Emission Relevant To Geochemical Exploration." *J. Geochem. Explor.*, v. 15, pp. 63–76, 1981.

Ball, T. K., Nicholson, R. A., Peachey, D., "Effects of Meteorological Variables On Certain Soil Gases Used To Detect Buried Ore Deposits." Trans., *Inst. Mining, Metallurgy, London*, v. 92, pp. B183–B190, 1983.

Adams, D. F., Farwell, S. O., Pack, M. R., Robinson, E., "Biogenic Sulfur Gas Emissions From Soils in Eastern and Southeastern United States," *J. Air Pollut. Control Assoc.*, v. 31, pp. 1083–1089, 1981.

Blackmer, A. M., "Diurnal Variability In Rate of Emission of Nitrous Oxide From Soils." *Soil Sci. Soc. Amer. J.*, v.46, pp. 937942, 1982.

Rightmire, C. T., "Seasonal Variation in P$_{co2}$ and $^{13}$C Content of Soil Atmosphere." *Water Res.* v. 14, pp. 691–692, 1978.

Klusman, R. W. and Landress, R. A., "Secondary Controls On Mercury in Soils of Geothermal Areas." *J. Geochem. Explor.*, v. 9, pp. 75–91, 1978.

Klusman, R. W., Cowling, S., Culvey, S., Roberts, C., Schwab, A. P., Preliminary Evaluation of Mercury and Arsenic In Soils of Selected Colorado Geothermal Districts." *Geothermics*, v. 6, pp. 1–8, 1977.

Klusman, R. W. and Matoske, C. P., "Adsorption of Mercury By Soils From Oil Shale Development Areas In the Piceance Creek Basin Of Northwestern Colorado." *Environ. Sci. Technol.*, v. 17, pp. 251–256, 1983.

Klusman, R. W. and Jaacks, J. A., "Environmental Influences Upon Mercury, Radon, and Helium Concentrations in Soil Gases At a Site Near Denver, Colorado." *J. Geochem. Explor.*, v. 27, pp. 259280, 1987.

Klusman, R. W., Voorhees, K. J., Hickey, J. C., Malley, M. J., "An Integrative Gas Geochemistry Technique for Surficial Petroleum Exploration." *Unconventional Methods In Exploration for Petroleum and Natural Gas-IV.*, M. J. Davidson, ed., Southern Methodist University Press, Dallas, pp. 219–243, 1986.

In addition to the methods already described, it is known that cryogenic trapping can be used as a concentration step with the low temperature reducing the rate of decomposition. However, cryogenic methods are logistically difficult or impossible in many environments where sampling is desired. This method is described in Farwell, S. O., Gluck, S. J., Bamesberger, L., Schutte, T. M., Adams, D. F., "Determination of Sulfur-containing Gases by a Deactivated Cryogenic Enrichment And Capillary Gas Chromatographic System." *Anal. Chem.*, V. 51, pp. 609–615, 1979.

A variety of adsorbents have been used for the collection of gases from the atmosphere and from soil gas. These include activated charcoal, molecular sieve, Tenax, and noble metal collectors for mercury and methyl mercury. Charcoal has been used in the accumulation of gases from petroleum deposits and described in U.S. Pat. Nos. 2,266,556, 2,284,147, and 4,573,454.

Molecular sieve materials have been used for the collection of selected soil gases and some of these methods have been described in Hinkle, M. D. and Dilbert, C. A., "Gases and Other trace Elements In Soils At the North Silver Bell Deposit, Pima County, Arizona." *J. Geochem. Explor.*, v. 20, pp. 323–336 1984. Wilmhurst used another molecular sieve material which was chemically plated with gold for the collection of vaporous mercury which is a method combining the uses of molecular sieve material to increase surface area, with noble metal for collection, and is described in "Sirosorb: A Collector For Use In The Determination Of Mercury In Geochemical Samples", Wilmhurst, J. R. and Ryall, W. R., *J. Geochem. Explor.*, v. 13, pp. 1–7, 1980. Dunkhase et al. used a specially prepared silver wire which was buried in the soil for periods of several weeks to collect mercury vapor from the soil pore space. This method is described in U.S. Pat. No. 4,565,786.

Tenax has been used to collect hydrocarbon vapors emanating from a contaminated groundwater and that material and method is described in "Volatilization of Organic Compounds From Unconfined Aquifers," Swallow, J. A. and Gschwend, P. M., *Proc.* 3rd National Symposium On Aquifer Restoration And Ground Water Monitoring, Columbus, OH, May 25–27, 1983, pp. 327–333.

Taufen has used the isotopic composition of soil gas in prospecting for sulfur deposits. Native sulfur deposits are produced in the subsurface by microorganisms utilizing indigenous organic matter or petroleum as a source of carbon and sulfate from gypsum or anhydrite as a source of oxygen. This method is described in "Taufen, P. M., Sulfur Gas Geochemical Prospecting" U.S. Pat. No. 4,377,640, 1983. Donovan et al., has described the use of carbon isotopes in the recognition of seepage of vapors from petroleum deposits in the publication "A Possible Petroleum-Related Geochemical Anomaly In Surface Rocks, Boulder and Weld Counties, Colorado", Donovan, T. J., Noble, R. L., Friedman, I., Gleason, J. D., *U.S. Geol. Survey, Open-file Rept.* 75-47, 11 p., 1975.

Liquids have been used for the collection of soil gases. Kanemasu, et al. (1974) described the use of potassium hydroxide solutions in the collection of carbon dioxide emitted from the soil surface. This is described in "Field Chamber Measurements of CO$_2$ Flux From Soil Surface", Kanemasu, E. T., Powers, W. L., Sij, J. W., *Soil Sci.*, v. 118, pp. 233–237, 1974. Rouse used a liquid for the collection of soil gases and is described in "Sulfur Gas Geochemical Detection of Hydrothermal Systems", Rouse, G. E., DOE/ID/12063, 27 p., 1984.

Additional prior disclosures of pertinent geophysical prospecting methods and apparatus for locating deposits in the earth are found in U.S. Pat. Nos. 2,112,845, 2,257,170, 2,465,563, 2,465,564 and 3,862,576.

SUMMARY AND OBJECTS OF THE INVENTION

The present invention relates to a method for collecting and analyzing reduced gases. A variety of gases are collected simultaneously, utilizing an integrative technique.

According to the invention, the gases can be collected as flux from the earth's surface into the atmosphere, from a water surface into the atmosphere, as soil gas in unsaturated soils, as soil gas in water-saturated or flooded soils, and at the sediment-water interface in water bodies.

Trace gases are collected for a period of 1-30 days, the period being determined by the gas(es) of interest, sensitivity desired, and experience in the particular application. The collection medium is an oxidizing liquid held in a novel container which allows entry of gases, but prevents entry of water or soil materials. After integration of the gas flux for the appropriate period of time, the collector is retrieved, sealed, and transported to a field laboratory or conventional chemical laboratory for analysis.

Gases which are in a dissolved, oxidized form in liquid are analyzed by a variety of techniques which are appropriate for the species of interest. For example, if methyl mercury were collected, the mercury would exist as the mercury (II) ion in the oxidizing liquid, and could be analyzed by atomic absorption spectrophotometry or by increase in electrical resistance in a gold film. If arsine or trimethylarsine were the collected gas, the arsenic would exist as the arsenate ion in the oxidizing liquid and could be reduced and analyzed by atomic absorption spectrophotometry or colorimetry. If the collected gas were hydrogen sulfide, or dimethyl sulfide, the collecting solution would contain sulfate, which could be analyzed by turbidimetric measurements or gravimetry.

If relatively large numbers of samples are collected and analyzed, a variety of statistical methods may be applied to aid in the interpretation of the data. Determination of statistical parameters such as mean, standard deviation, and range would be appropriate. Analysis of the distribution of the concentrations in a data set through other techniques will allow the recognition of samples of anomalously high concentrations of the gas of interest. If more than one species is being determined, multivariate statistics can aid in determining the relationship of one collected species to another, and in the interpretation of the processes being studied.

The data for multiple sample stations can be plotted on a map which is representative of the area being studied. Contouring of areas of equal concentration (isopleths) will aid in the interpretation of the data and of the processes occurring in an area of interest.

Applications of the present invention are numerous and only a few will be presented as illustrative of the application to mineral exploration and to environmental studies. The descriptions which follow describe how the present invention overcomes problems in the prior art and promotes extension of the applications of vapor geochemistry in fields where it has the most promise.

The exploration for large tonnage, low-grade gold deposits is being actively pursued in several areas of the western United States and Pacific Rim countries. The gold contained in these disseminated deposits is extremely fine-grained and not visible to the naked eye or under low magnification. An important method of exploration, therefore, is the analysis of large numbers of samples of outcropping rock or soil samples for gold and other elements, such as arsenic, mercury and antimony which are useful as an indicator of gold, frequently being termed pathfinder elements. Most gold deposits with surface expression have been found and there is a need to employ methodology and apparatus which can detect the occurrence of such deposits buried under alluvium and volcanic rock cover, and which have no surface expression.

The use of vapor or gas geochemistry has not been widely applied to the pursuit of gold deposit exploration. There has been previous application of mercury vapor geochemistry to the exploration for disseminated gold deposits with limited success because of the lack of understanding of the complexities of vapor migration and adsorption of the gases in the overlying soil column. The use of mercury vapor has fallen into disfavor because of the complications in its application.

More recently, the use of carbon dioxide or carbon dioxide ratioed to oxygen has been applied to gold exploration. A limited amount of this data has been published, and there are suggestions that the method works effectively only during a certain season of the year. In this method, the infiltration of meteoric water during the late spring in dry climates initiates the production of carbon dioxide in the zone of shallow oxidizing ore bodies which may allow the detection of a change in the carbon dioxide to oxygen ratio in a shallow soil gas sample.

Until the present invention, the potential for use of arsenic, antimony, or sulfur vapor geochemistry has not been realized in the undertaking of finding gold deposits. The biomethylation of these chemical elements produces vapors of limited stability and their direct collection and measurement has been detected only where the appropriate methyl analog is applied directly to the soil. The high concentrations of arsenic, antimony, mercury, and sulfur commonly associated with the reduced portions of gold deposits may be subject to biomethylation at the boundary between reduced and oxidizing conditions in the ore body. The biomethylation will occur under the right conditions of temperature, moisture, and low concentrations of oxygen dissolved in the porewaters.

By using the collectors of the present invention, buried in the soil at a shallow depth for an appropriate collection time, gases such as methylsulfide, dimethylsulfide, arsine, dimethylarsine, trimethylarsine, and the antimony analogues, which have migrated toward the surface can be collected, preserved in the oxidized form and analyzed. Having knowledge of the distribution of reduced sulfur, arsenic and antimony gas species over the area of interest will be an aid to the discovery of covered gold deposits.

Platinum group metals, including platinum and palladium occur in rocks commonly described as ultramafic. These types of rocks are relatively unusual, and occur in the oldest portions of the earth's crust. Although the rock types are readily recognized, the presence and particularly the distribution of platinum group metals is exceedingly difficult to define. In areas where there are no outcrops, the exploration for the platinum group metals is difficult and expensive. The platinum group metals are frequently associated with sulfide minerals such as pyrrhotite, pyrite, and pentlandite. There may or may not be arsenic-containing minerals closely associated with the platinum group metals. The weathering of the sulfide-containing minerals produces volatile sulfur-containing gases such as carbonyl sulfide, methyl sulfide, dimethyl sulfide, or carbon disulfide, encouraging the use of the collector of the present invention buried in the soil above areas being prospected for the platinum group metals and collecting the sulfur-containing gases as the sulfate ion and any volatile arsenic compounds as the arsenate ion in the oxidizing solution. Detection of the sulfate and/or arsenate ion can be an indicator of possible platinum group metal ore in the subsurface. The present invention provides a new and unique method for improved exploration effectiveness for the platinum group metals in areas of ultramafic rocks.

An example of an environmental application of the present invention is determining the selenium toxicity produced by the irrigation of areas containing selenium-rich soils. The best-known example of the problem caused by this contamination is the deformities noted in waterfowl of the Kesterson Wildlife Refuge in California where a large scale irrigation project is providing water to arid land in the San Joaquin Valley and drainage from this irrigated land is high in dissolved selenium which is derived from seleniferous shales in the irrigated area. The Wildlife Refuge is the sump for irrigation return flow and receives the high selenium water.

A potential re-mediation process for this area is biomethylation of selenium in the water-logged soils, which is likely occurring naturally. Heretofore, the detection and measurement of the rate of bio-methylation was difficult because of the low stability of the methylated species of selenium and detection limit problems in the analysis of methylated selenium. The present invention will, however, allow the collection of methylselenium and dimethylselenium, converting it to the stable selenate ion in the oxidizing solution. In this way, the difficulty of preserving the relatively unstable methylated species of selenium is overcome as only the vapor forms can enter the collector. The collector can be placed in dry or water-logged soils, floated on ponds, or anchored at the water-sediment interface at the bottom of ponds. This methodology will allow the determination of rates of biomethylation of selenium and estimates of times required for natural re-mediation.

Artificial, or constructed wetlands are presently being evaluated for use in the low-cost remediation of acid mine drainage. One of the processes operating in a wetland is sulfate reduction. Microbes operating in an anaerobic environment reduce sulfate in the mine drainage to hydrogen sulfide which is partially lost to the atmosphere. The other portion dissolves in the water to produce bisulfide ion which precipitates metals as insoluble sulfides. The present invention provides a means for the collection of the reduced gas hydrogen sulfide and can serve as an indicator of the effectiveness of the wetland in the treatment of acid mine drainage. Previous methods of collection of hydrogen sulfide in the study of sulfate reduction relied upon the cryogenic trapping of the gas or direct precipitation of a metal sulfide in a solution.

It is therefore the primary objective of the present invention to provide a simple, low-cost, novel, but effective means for the collection of reduced gases in any environment.

Another object is to provide improved methodology for the exploration for underground deposits of economic interest.

A further object is to provide new methodology for the study of processes of environmental significance.

Other and still further objects, features and advantages will become apparent upon a reading of the following detailed description of the invention taken in conjunction with the accompanying drawings in which:

FIG. 1 is a perspective view of the integrative collector of the present invention in the open position which enables gases to enter the interior thereof through the apertures shown in the threaded plug in the top portion of the collector vessel.

FIG. 2 is a perspective view of the collecting vessel with the threaded plug shown removed to reveal the construction of the vessel's interior.

FIG. 3 is a perspective view of the collector of the present invention where the plug is shown in the closed position, sealing the oxidizing liquid with any dissolved oxidized gas species in the container for transport to an analyzing laboratory.

FIG. 4 is a cross-sectional view taken along lines 4—4 of FIG. 1 and showing the oxidizing liquid and glass wool deposited in the interior of the container.

FIG. 5 is a cross-sectional view taken along lines 5—5 of FIG. 3.

FIG. 6 is a fragmentary cross-sectional view of a section of underground soil, showing the integrative collector in the open position and submerged under the surface of the soil with a conical cover providing an open space around the collector permitting the adsorption of gases from the surrounding soil pore space.

FIG. 7 is a fragmentary perspective and cross-sectional view of an area of land showing a plurality of the collectors of the present invention buried at a shallow depth in the soil in a grid pattern in order that the collectors can operate to determine the relative or absolute flux of gases of interest of an area of study.

FIG. 8 is a side view, shown partially in cross-section, of the collector of the present invention, in the open position, floating on a water body and secured under a conical cover, allowing gas or gases to enter the collector which are exsolving from the water body.

FIG. 9 is a fragmentary cross-sectional view of the integrative collector disposed at the bottom of a water body and held under a weighted conical cover by a screen material which holds the collector beneath the cone and is connected to the surface by a float, allowing gases to enter the collector which are exsolving from the sediment at the bottom of a water body.

DETAILED DESCRIPTION OF THE PREFERRED EMBODIMENTS

The collector 2 of the present invention, illustrated in detail in FIGS. 1-5, is constructed of a cup 3 having a cylindrically shaped interior with threaded side walls 5. The threads of the side walls engage the threads 6 of a cylindrical plug 7 which is adapted to be screwed into the cup to provide air and liquid tight closure of the cup's interior when the plug is fully seated, as shown in FIGS. 3 and 5. When the plug 7 is only partially screwed into the cup 3, a series of radially bored coplaner apertures 9 in the plug 7 are exposed above the top lip of the cup 3, as shown in FIGS. 1 and 4. The plug 7 is configured as an inverted cup with a top portion 10 and depending cylindrical side walls through which the aperture 9 are drilled to provide gaseous communication between the interior of the cup and the outside environment when the plug is in the partial position shown in FIGS. 1 and 4. Radial slots cut into the bottom portion of the depending side walls of the plug 7 would be a suitable alternative to the drilled holes 9.

The collector 2 is prepared for use by washing and rinsing with demineralized water in the same fashion as cleaning any chemical glassware or plastic-ware. A predetermined amount of clean, high-quality glass wool 12, suitable for chemical use, is placed in the collector, together with a quantity of oxidizing liquid 14. Other materials which increase the surface area of the oxidizing liquid may also be used, such as fibrous wick. The plug 7 is tightened into the cup 3 to prevent dirt or other foreign material from entering the clean detector and to prevent loss of the liquid 14 during transport to or from the field.

The oxidizing liquid 14 may be one of several suitable for the specific application. Examples, but not a complete list include sodium hypochlorite, calcium hypochlorite, aqueous hydrogen peroxide, and sodium peroxide. Factors which will influence the appropriate choice for a particular application include: cost, ease of transportation to the field in a dry or liquid form, necessity of refrigeration during transport, strength or oxidizing power, maintenance of oxidizing capability over a gas collection period of several weeks, and the solubility of the collected, oxidized species in the solution.

If an oxidizing agent in the dry form is taken to the field, provision must be made for weighing at the field location or preweighed packets can be taken to the field. The advantage of the dry form is the decreased risk of spillage and less weight to transport. Batches of the oxidizing liquid can be made up in the field, and the collectors filled by means of a dispensing device such as a pipeter.

The strength of the oxidizing agent varies, with calcium hypochlorite being a stronger oxidizing agent than sodium hypochlorite, if at the same molarity. Calcium hypochlorite is also more stable and more soluble in water. Thirty percent aqueous hydrogen peroxide is stronger than ten percent hydrogen peroxide. The appropriate oxidizing agent and its concentration is the field application must be determined empirically.

The solubility of the collected species is an important consideration in choice of an oxidizing agent and its concentration in the collector. If reduced gases containing arsenic are of interest and are to be collected by calcium hypochlorite, the solubility of calcium arsenate is a limiting factor. If the calcium hypochlorite concentration is 1.0M in the collector, the maximum amount of arsenic containing gas which could be collected in 50 ml of liquid without precipitation of solid calcium arsenate would be 12.2 mg as arsenic at 25 degrees Celsius and without correction of the solubility for ionic strength. If sulfur containing gases are to be collected, the species in the solution will be sulfate, and only 0.12 mg of sulfate could be collected without precipitating calcium sulfate. The precipitation of a solid in the glass wool or wick would present difficulties in resolubilizing for analysis. The complete recovery of the liquid and dissolved constituents is critical for successful application. The crystallization of any solid could result in loss of other constituents of interest due to co-precipitation and adsorption. In most applications, a multiplicity of gases are adsorbed by the liquid and the solubility of all potential solids must be considered.

In field use where gas is to be collected from shallow soil depths, as illustrated in FIGS. 6 and 7, a hole 22 is dug or augured in the soil 20 for placement of the collector 2. The depth of the hole is determined by the equipment available for placement, the physical condition of the soil, and the stability of the reduced gas in the soil column. The concentration of reduced gases increases with depth in most natural systems, with concentration discontinuities occurring at the water table. A compromise of all of the above parameters is usually necessary. It is important that the depth of the placement of collectors be as constant as practical in a given study.

FIG. 7 illustrates a configuration for the placement of collectors in a field area for subterranean gas collection. A multiplicity of collectors can be placed in a variety of patterns such as square grids, rectangular grids, triangular or hexagonal grids, or along lines. The spacing between collectors is a function of the nature of the study, the resolution desired, and the experience of the investigator in the particular application.

After the appropriate time of integrative collection of gases by the collector, the collectors are retrieved. Significant evaporation and loss of the oxidizing liquid will not occur, except in applications where the collection system is above the soil or water surface. Direct exposure to higher temperatures on the surface can result in evaporation or loss of oxidizing capability of the liquid. This must be considered in the selection of time of integrative collection.

The data from the determination of one or more volatile constituents of interest from a multiplicity of samples can be interpreted in a variety of ways. The presence of substantial concentrations of a given volatile constituent can allow the investigator to ascertain the existence of a particular natural or man-influenced process in an area. Simple statistics can be used to quantify the magnitude of such processes and to compare with other areas or with measurements at the same locations for different time periods and seasons. Multi-variate statistics can be used to compare and interpret data for multiple constituents measured by the present invention or by other methods of collection and analysis. The coordinates of the samples can be used to plot the location of the samples with the concentration of one or more constituents plotted at the appropriate coordinates. The resultant map of the data can be interpreted directly or contoured to show areas of equal concentrations. The resultant maps can be used to estimate differences in rates of certain processes which can be of value in the study of the environment or in the search for underground deposits of economic interest.

A wide range of reduced gases may be collected if present in the environment. Table 1 is a non-exhaustive list of gases which may be collected by the present invention, and the chemical form which likely occurs for these gases in the oxidizing liquid. A variety of individual gas species may be possible, but there is a partial loss of the identity as the gases dissolve in the oxidizing liquid. Using arsenic as an example, arsine, methylarsine, dimethylarsine, and trimethylarsine are possible gas species present in the natural environment. The oxidizing liquid will convert all of these species to arsenate ion and the individual identity will be lost. The analytical determination of arsenic will result in a measure of the total volatile arsenic collected at the field location.

The analytical method used for the determination of the volatile element(s) of interest is a function of the element, sensitivity desired, and availability of equipment.

TABLE 1

Possible Gases of Interest and Oxidized Aqueous Form.

| Gas Species | Oxidized Aqueous Forms |
|---|---|
| mercury | mercuric ion |
| dimethylmercury | mercuric ion |
| thallium hydride | thallic ion |
| methylthallium | thallic ion |
| tetramethylgermanium | germanate ion |
| dimethyltin | stannate ion |

TABLE 1-continued

Possible Gases of Interest and Oxidized Aqueous Form.

| Gas Species | Oxidized Aqueous Forms |
|---|---|
| tetramethyltin | stannate ion |
| dimethyllead | plumbate ion |
| arsine | arsenate ion |
| methylarsine | arsenate ion |
| dimethylarsine | arsenate ion |
| trimethylarsine | arsenate ion |
| stibine | stibnate ion |
| methylstibine | stibnate ion |
| dimethylstibine | stibnate ion |
| trimethylstibine | stibnate ion |
| bismuth hydride (bismuthine) | bismuthate ion |
| methylbismuth (methylbismuthine) | bismuthate ion |
| dimethylbismuth (dimethylbismuthine) | bismuthate ion |
| trimethylbismuth (trimethylbismuthine) | bismuthate ion |
| hydrogen sulfide | sulfate ion |
| methyl sulfide (methylhydrosulfide) | sulfate ion |
| dimethyl sulfide | sulfate ion |
| dimethyldisulfide | sulfate ion |
| carbonyl sulfide | sulfate ion |
| carbon disulfide | sulfate ion |
| hydrogen selenide | selenate ion |
| methylselenide (methylhydroselenide) | selenate ion |
| dimethylselenide | selenate ion |
| dimethyldiselenide | selenate ion |
| hydrogen telluride | tellurate ion |
| methyltelluride (methylhydrotelluride) | tellurate ion |
| dimethyltelluride | tellurate ion |

The present invention may be embodied in other specific forms without departing from the essential characteristics or the spirit of the invention.

In operation, the collector 2, filled with liquid 14 and glass wool 12, is placed in the hole 22 with the plug 7 in the open position, exposing the apertures 9 to the below ground environment. The collector is covered with a shielding cone 24 or other form of covering which can be made of plastic or thin sheet metal, such as aluminum. The hole is back-filled with soil leaving an air space under the cone 24 for collection of soil gas which is adsorbed by the pooled oxidizing liquid in the cup 3 and the liquid which covers the surface of the glass wool or wick 12. The size of the cone may be of importance for flux studies, in that it intercepts the upward migrating gases from a fixed known area and a constant sized cone for all of the collectors in a given area is important. The collector is left in the soil to integrate the soil gas flux for a period of time that is determined to be appropriate based on the experience of the investigator. When the collector 2 is retrieved, the plug 7 is screwed tightly to its full depth to isolate the sample and prevent loss of the oxidizing liquid until it is removed in the laboratory for analysis.

In the application shown in FIG. 8, the objective is to collect gases emanating from a water surface. The open collector 2 is supported on a wire or nylon mesh screen 27 which is secured to the covering cone 24 by wires or cables 29 trained through an eyelet 30 in the apex of the cone and terminating in anchoring eyelets 32 in the perimeter of the mesh screen 27. The size of the mesh is not critical to the application, although a mesh finer than two millimeters is not recommended, in that it can prevent gas bubble migration through the mesh because of surface tension. The apparatus will trap enough air to float if the conical section 24 is tight and does not leak air from its top. The entire assembly can be held in position by an appropriate anchoring device (not shown). Retrieval and collection are accomplished similarly to the underground application described earlier.

FIG. 9 illustrates the application of the present invention to the collection of gases from the sediment water interface at the bottom of a shallow water body. The configuration of the assembly is similar to the water application described in connection with FIG. 8 in that the collector 2 is supported in place under a cone 24 by the floor mesh 27. In this case, the assembly must be weighted (not shown) to hold it on the bottom. A small float 30 attached to the cone is used only for location of the submerged gas collectors 2. The float 30 must not lift the collector off from the bottom, and the float must not be so large to cause significant wind resistance which will drag the assembly along the bottom.

Deep water applications are more complex. As the assembly is lowered, air or an inert gas must be continually added to the cone to compensate for compression of the air in the conical space. If compression reduces the gas volume under the cone, the collector could become flooded with water during the descent. This compensation can be done by release of inert gas from a small gas cylinder that is part of the apparatus (not shown). The amount released is controlled by an external pressure sensor. In this case, a float is not used, but a collapsed balloon is attached to the collector which will be inflated by remote acoustic signal at the time of desired collection. In both the shallow and deep water application, the time appropriate for gas collection is determined empirically.

I claim:
1. Apparatus for the integrative collection of reduced gases, including:
   a container body having an opening, and including within the container, a quantity of oxidizing liquid; and wick means immersed in the liquid to absorb the oxidizing liquid and thereby increase the surface area of the liquid;
   plug means sized and adapted for insertion into the opening and including means for raising and lowering the plug means within the opening between given dimensional limits;
   selectively open aperture means through the plug means operative as a function of the travel of the plug means between the said dimensional limits.
2. The combination of claim 1 wherein the means for raising and lowering the plug means are screw threads and further including cooperative screw threads carried by the container and disposed in the opening.
3. The method of collecting reduced gases, including, isolating a quantity of oxidizing liquid in a container which is constructed to permit selective gaseous communication with an outside environment;
   situating the container within a medium containing the gases to be collected and within an airspace contiguous to the medium;
   selectively opening said container to gaseous communication with said outside environment for collecting gases;
   oxidizing said collected gases in said oxidizing liquid;
   storing said oxidized gases in aqueous form.
4. The method of claim 3 and further including the step of placing a fibrous material into the oxidizing liquid so that by capillary action the material is wetted and increases the surface area of the oxidizing liquid.
5. The method of claim 4 and further including the steps of removing the container from the medium and sealing the container against movement of gas and liquid.

6. The method of claim 4 wherein the medium is earth soil.

7. The method of claim 6 and further including the step of situating a plurality of the described containers over an area of land placed one from another in a pattern and at a constant depth.

8. The method of claim 4 where the medium is a water body.

* * * * *